United States Patent

Benazzi et al.

[11] Patent Number: 5,908,967
[45] Date of Patent: Jun. 1, 1999

[54] CATALYST BASED ON A MORDENITE ZEOLITE MODIFIED WITH CERIUM, AND ITS USE IN THE ISOMERISATION OF AN AROMATIC C8 CUT

[75] Inventors: Eric Benazzi, Montesson; Fabio Alario, La Varenne; Christian Marcilly, Houilles, all of France

[73] Assignee: Institut Francais du Petrole, France

[21] Appl. No.: 08/686,061

[22] Filed: Jul. 24, 1996

[30] Foreign Application Priority Data

Jul. 24, 1995 [FR] France ................... 95 09058

[51] Int. Cl.[6] .............. C07C 5/25; C10G 35/09; C10G 35/095
[52] U.S. Cl. .......... 585/481; 585/482; 208/137; 208/138; 208/141
[58] Field of Search .................. 585/480, 481, 585/482; 208/137, 141, 138

[56] References Cited

U.S. PATENT DOCUMENTS

| 3,644,200 | 2/1972 | Young ................. 208/120 |
| 3,907,914 | 9/1975 | Willis, Jr. et al. ........... 260/668 A |
| 3,917,565 | 11/1975 | Michlmayr ................. 208/144 |
| 3,917,739 | 11/1975 | Parthasarathy et al. ........ 260/683.65 |
| 3,923,639 | 12/1975 | Ciric ......................... 208/111 |
| 4,162,214 | 7/1979 | Maslyansky et al. ............ 585/471 |
| 4,323,481 | 4/1982 | Kaduk ..................... 252/455 Z |
| 4,665,272 | 5/1987 | Bakas et al. .................. 585/739 |
| 4,861,740 | 8/1989 | Sacthler et al. ................ 502/66 |

FOREIGN PATENT DOCUMENTS

| 0 559 021 | 9/1993 | European Pat. Off. . |
| 2 134 425 | 12/1972 | France . |

*Primary Examiner*—Bekir L. Yildirim
*Attorney, Agent, or Firm*—Millen, White, Zelano & Branigan, P.C.

[57] ABSTRACT

The invention concerns a process for the isomerization of an aromatic C8 cut using a catalyst containing mordenite, cerium and at least one metal from group VIII. It also concerns a catalyst containing 2–98% by weight of mordenite, 7–40% by weight of cerium, and 0.01–3% by weight of at least one metal from group VIII, the cerium being deposited on the mordenite, and the percentages being with respect to the weight of catalyst.

15 Claims, No Drawings

CATALYST BASED ON A MORDENITE ZEOLITE MODIFIED WITH CERIUM, AND ITS USE IN THE ISOMERISATION OF AN AROMATIC C8 CUT

BACKGROUND OF THE INVENTION

The present invention concerns a catalyst and a process for the isomerization of an aromatic C8 cut. The catalyst of the invention is an aluminosilicate comprising a mordenite zeolite in which the selectivity and/or catalytic properties has been modified by selectively deactivating the external crystal surface by forming a layer of cerium oxide on the surface, and comprising at least one metal from group VIII of the periodic classification of the elements (Handbook of Chemistry and Physics, 65th edition, 1984–85), and a matrix. In general, the external surface of zeolite crystals is modified by dry impregnation of mordenite by an alcoholic or aqueous solution of a cerium salt.

Commercial catalysts currently used for the isomerisation of aromatic C8 cuts are essentially based on ZSM5 zeolite (U.S. Pat. No. 4,482,773, for example).

ZSM5's importance lies in its excellent form selectivity, leading to high selectivity for para-xylene; the selectivity regarding undesirable secondary dismutation reactions remains at a very low level.

Other zeolites with larger pore openings of 12MR (an opening the size of 12 oxygen atoms) have also been used, such as mordenite. Mordenite based catalysts are particularly described in U.S. Pat. No. 4,723,051. However, these zeolites do not have particular geometrical selectivity properties. This means that, whatever its Si/Al ratio, para-xylene selectivities are lower than those obtained for ZSM5 zeolite and in particular, leads to higher production of trimethylbenzene. The production of trimethylbenzenes by dismutation is actually encouraged in mordenite where the microporous system is more open than that of ZSM5: the openings are the size of 12 oxygen atoms instead of 10 for ZSM5.

We have researched improved catalysts based on mordenite to reduce side reactions, in particular the production of trimethylbenzene.

SUMMARY OF THE INVENTION

We have discovered that catalysts containing cerium favor xylene isomerization.

Catalysts containing mordenite exchanged with cerium (0.08–4%), platinum or palladium are known for the isomerisation of n-paraffins from U.S. Pat. No. 3,917,739. However, they have never been described for the isomerisation of xylenes.

An object of the present invention is to provide a process for the isomerization of an aromatic C8 cut containing xylenes, using a catalyst comprising a matrix, mordenite, cerium wherein the content of cerium is 0.1–40% by weight of the total catalyst and at least one metal from group VIII.

A further object of the present invention is to provide a catalyst comprising a matrix, mordenite on which 7–40% by weight (with respect to the total catalyst weight) of cerium, and at least one metal from group VIII (preferably a noble metal, advantageously palladium and/or platinum) has been deposited.

Further, we have surprisingly discovered that by impregnating (preferably dry impregnating) mordenites with organic solutions, preferably alcoholic solutions, or aqueous solutions of at least one cerium compound (preferably a salt), it is possible to obtain catalysts based on mordenite and a metal from group VIII which are active and selective in the isomerization of C8 aromatics.

This novel preparation procedure confers greatly improved selectivity properties on the treated mordenite, in which the external crystal surface has been inhibited. This results in surprising inhibition of undesirable secondary reactions such as the dismutation reaction, and also in a slight reduction in its activity which is not, however, prejudicial to the yield of the catalyst based on modified mordenite of the present invention. This novel mordenite results in selectivities towards dealkylation side reactions which are lower than those of catalysts based on ZSM5. The solids obtained exhibit C8 aromatic isomerization performance which is not only better than those of prior art mordenites but also are at least equivalent, or even better, than the performance of ZSM5 based catalysts.

The mordenite used in the catalyst of the present invention is produced either from a small pore mordenite or from a large pore mordenite, synthesized in either a hydroxide or in a fluoride medium.

Small pore mordenite has a sodium content, with respect to the weight of dry mordenite, which is generally in the range 4% to 6.5%, a global Si/Al atomic ratio which is generally in the range 4 to 7, and an elemental cell volume which is generally in the range 2.76 $nm^3$ to 2.80 $nm^3$ (1 $nm=10^{-9}$ m). It normally only adsorbs molecules with a kinetic diameter of less than about $4.4\times10^{-10}$ m.

Large pore mordenite, synthesized in an $OH^-$ medium or in a fluoride medium, for example as described in European patent EP-A-4,275,579, is distinguishable from the small pore type by the fact that it can adsorb molecules with a kinetic diameter of more than about $6.6\times10^{-10}$ m, and thus in particular benzene molecules, and its global Si/Al atomic ratio is generally in the range 4.5 to 12.

Before rendering the mordenite selective by dry impregnation with aqueous or alcoholic solutions of cerium compounds (salts), it may be necessary to bring the global Si/Al ratio of the mordenite to values which are greater than those obtained on synthesis and mentioned above, i.e., an Si/Al ratio of more than 12 in the case of large pore mordenites and 7 in the case of small pore mordenites. Any technique which is known to the skilled person can be used to obtain dealuminized mordenites over a wide range of Si/Al ratios, for example direct acid attack, calcining the $NH_4^+$ form in the presence or otherwise of steam followed by one or more acid attack steps, or "calcining-acid attack" cycles. In the specific case of small pore mordenite, it should be ascertained that the treatments used do lead to channel opening.

The mordenite selectivity is modified by dry impregnation with cerium salt solutions, preferably using large pore mordenites with a Si/Al ratio in the range 4.5 to 100, preferably in the range 4.5 to 45, and more preferably in the range 4.5 to 20. When small pore mordenites are used, the Si/Al ratio is about 4 to 100, preferably 4 to 45, and advantageously 4 to 7. The mordenites are in the $Na^+$, $H^+$ or $NH_4^+$ form or in any mixed form which is a combination of these three, preferably the $NH_4^+$ form. The $NH_4^+$ form is produced either using crude synthesized mordenite in its sodium form and carrying out a number of ion exchange runs using concentrated ammonium nitrate (10N) solutions to obtain a sodium content with respect to the weight of dry mordenite of generally less than 2000 ppm by weight, preferably 1000 ppm by weight and more preferably 500 ppm by weight, or by using dealuminated mordenites, and carrying out several successive exchange runs using ammonium nitrate to produce the $NH_4^+$ form of the zeolite.

The catalytic properties of mordenite samples are modified using a procedure which comprises three steps.

The first step consists of calcining the mordenite in its $NH_4^+$ form at a temperature of 450° C. to 550° C. in dry air or a dry inert gas.

The second step consists of dry impregnation of the mordenite using a cerium salt solution, non limiting examples of which are: $Ce(CH_3COO)_3$, $Ce(CH_3COO)_3 \cdot 1.5H_2O$, $Ce(NO_3)_3 \cdot 6 H_2O$, $Ce(OH)(NO_3)_3 \cdot 3 H_2O$, Ce(III) salicylate with chemical formula $Ce(C_7H_5O_3)_3)$, and (Ce(III)-2,4-pentanedione with chemical formula $Ce(C_5H_7O_2)_3)$. The solvent used to dissolve the cerium salts is one which will achieve the highest solubilities. A complexing agent may be added to the solvent, such as citric acid. The solvent is either water or an organic solvent, preferably ethyl alcohol or water. After the impregnation proper, the solid is dried, for example at 100° C. in a ventilated oven for a period of 4 to 24 hours, preferably 4 to 12 hours.

The third step consists of calcining the mordenite in dry air, which mordenite has been impregnated with a cerium solution and dried, at a temperature in the range 350° C. to 600° C., preferably in the range 450° C. to 550° C. in dry air for a period in the range 4 hours to 36 hours, preferably in the range 5 hours to 12 hours.

It should be noted that the complete cycle comprising steps 1, 2 and 3 can be carried out as many times as is necessary. It is also possible to carry out several cycles comprising only steps 1 and 2, a final calcining step 3 being carried out after the last cycle is completed.

In a first variation of the preparation, the zeolite can then have deposited on it at least one metal from group VIII, preferably selected from the group formed by platinum and palladium, followed by forming using any technique which is known to the skilled person. In particular, it can be mixed with a matrix, generally an amorphous matrix, for example damp alumina gel powder. The mixture is then shaped, for example by extrusion through a die.

In the remainder of the text, the mixture of mordenite+ matrix will be termed the support.

Forming can generally be carried out with matrices other than alumina such as magnesia, silica alumina, clays (for example kaolin, bentonite) and techniques other than extrusion, such as pelletization or bowl granulation. The matrix, e.g., alumina, generally amounts to 1.89–90.99%, preferably 15–85% by weight of the catalyst.

In a second preferred variation of the preparation, the mordenite loaded with cerium is mixed with the matrix (as described above, in the proportions given) then a hydrogenating metal from group VIII, preferably Pt and/or Pd, can be deposited on the support, before or after forming, using any procedure which is known to the skilled person which can deposit metal on the mordenite. Competitive cation exchange can be used, where the competitor is preferably ammonium nitrate, the competition ratio being at least about 30, advantageously about 50 to 200. In the case of platinum or palladium, a platinum tetramine complex or a palladium tetramine complex is usually used: practically all of these latter deposit on the mordenite. This cation exchange technique can also be used to deposit the metal directly onto mordenite powder, before mixing with any matrix.

In a third preferred variation, the mordenite loaded with cerium is mixed with the matrix. The group VIII metal(s) (preferably platinum and/or palladium) are then no longer directly deposited on the mordenite but on the matrix, before or after the forming step, using anionic exchange with hexachloroplatinic acid, hexachloropalladic acid and/or palladium chloride in the presence of a competing agent, for example hydrochloric acid. In general, after depositing the platinum and/or palladium, the catalyst is calcined as above then reduced in hydrogen as indicated above.

Finally, in a final variation, the mordenite charged with cerium is mixed with a matrix onto which at least one metal from group VIII has been deposited (using the techniques described), then the mixture is formed.

Deposition of the metal (or metals) from group VIII is generally followed by calcining in air or oxygen, usually at 300° C. to 600° C. for 0.5 to 10 hours, preferably at 350° C. to 550° C. for 1 to 4 hours. This can then be followed by reduction in hydrogen, generally at a temperature in the range 300° C. to 600° C. for 1 to 10 hours; preferably, a temperature of 350° C. to 550° C. is used for 2 to 5 hours.

The catalyst obtained contains 2% to 98% (preferably 3–90%) by weight of mordenite with respect to the total catalyst weight, 0.1% to 40% (preferably 0.2–25%) by weight of cerium with respect to the total catalyst weight and 0.01% to 3% (preferably 0.02–2%) by weight of metal (metals) from group VIII with respect to the catalyst weight, as well as 1.89–97.89%, preferably 15–85% by weight of a matrix with respect to the weight of the catalyst.

A preferred catalyst contains 7–40% by weight of cerium, preferably 7–25% by weight, the cerium having been deposited on the mordenite, preferably by dry impregnation. The catalyst preferably contains no halogens.

The bifunctional catalyst obtained using the above procedures is used for the isomerization of an aromatic C8 cut, in particular of cuts containing xylenes (ortho and/or meta and/or para), comprising, for example, either a mixture of xylenes alone, or a mixture of xylene(s) and ethylbenzene. The isomerization of alkylaromatics, in particular xylenes, is of considerable commercial importance. Generally, para-xylene is the most desirable product, as it is for particular use as an intermediate in the manufacture of polyester fibers. Preferably, para-xylene is manufactured by isomerizing meta-xylene, which itself can be obtained by the isomerization of ortho-xylene. Ethylbenzene, which is difficult to separate from a xylene mixture by distillation (the boiling points of the different compounds are very close together), is often found in the feed for the isomerization of aromatic C8 hydrocarbons.

The operating conditions of a process for the isomerization of an aromatic C8 cut carried out in the presence of at least one catalyst of the invention are as follows:

temperature in the range 240° C. to 600° C., preferably in the range 350° C. to 510° C.;

pressure in the range 0.05 MPa to 10 MPa, preferably in the range 0.2 MPa to 3 MPa;

space velocity (wwh, weight of feed per unit weight of catalyst per hour) in the range 0.5 $h^{-1}$ to 200 $h^{-1}$, preferably in the range 2 $h^{-1}$ to 100 $h^{-1}$;

molar ratio of hydrogen to hydrocarbons in the feed ($H_2$/HC) in the range 0.5 to 12, preferably in the range 2 to 6.

The following examples illustrate the invention without in any way limiting its scope: they are given for a feed formed by 80% of ortho-xylene and 20% of ethylbenzene (% by weight).

EXAMPLES

Example 1: Catalyst C1, in accordance with the invention

The raw material was a large pore mordenite with a global Si/Al ratio of 5.2, a lattice Si/Al ratio, measured using infra-red, of 5.3, a sodium content with respect to the weight of dry mordenite of about 4.2%, an elemental cell volume of 2.794 nm$^3$, a pore volume in nitrogen, measured at $-196°$ C. and at $P/P_0=0.19$, of 0.163 cm$^3$ of liquid per gram of mordenite, and a specific surface area, measured by the B.E.T. method, of 370 m$^2$/g.

The mordenite firstly underwent 3 ion exchange runs in a solution of 10N NH$_4$NO$_3$ at about 100° C. for 4 hours for each exchange run. The weight content of sodium measured after this treatment was less then 50 ppm.

The NH$_4^+$ form of mordenite obtained above was then calcined in dry air for 4 hours at 500° C. 50 g of the prepared mordenite was then dry impregnated with 60 ml of an ethanolic solution containing 19.4 g of the salt Ce(NO$_3$)$_3$.6H$_2$O. The operations described above were then repeated once more. Finally, the modified mordenite was calcined in dry air at 550° C. for 4 hours.

The solid obtained following these treatments was given the reference HMCe1. The cerium content was 25% by weight with respect to the zeolite.

The latter was intimately mixed with alumina on which 0.3% by weight of platinum had been dispersed. The product constituted by the mixture of HMCe1 mordenite+alumina contained 40% by weight of alumina. The platinum content in the final catalyst (containing HMCe1) was thus about 0.12% by weight.

The catalyst produced was then formed by pelletization, calcined in air at 550° C. for 2 hours and reduced in hydrogen at 500° C. for 3 hours.

Catalyst C1 produced was tested by isomerization of a mixture of ortho-xylene (80% by weight) and ethylbenzene (20% by weight) at a pressure of 1.2 MPa, a space velocity (wwh) of 10 (hour)$^{-1}$ and a hydrogen to hydrocarbons ratio (H$_2$/HC) of about 4.

The performance of catalyst C1 (and the catalysts prepared in the following examples), shown in Table I, is defined as:

Approximate equilibrium of o-xylene (AEQ-ox) (%) =

$$\frac{\% \text{ of o-xylene/xylenes in feed} - \% \text{ of o-xylene/xylenes in effluent}}{\% \text{ of o-xylene/xylenes in feed} - \% \text{ of o-xylene/xylenes at equilibrium}} \times 100$$

Yield of C8 aromatics (%) =

$$\frac{\text{mass of C8 aromatics and naphthenes in receptacle}}{\text{total mass of C8 aromatics in feed}} \times 100$$

Dismutation selectivity (%) =

$$\frac{\text{mass of trimethylbenzene} + \text{mass of benzene}}{\text{mass of products}} \times 100$$

Example 2: Catalyst C2, in accordance with the invention

The raw material used was the same mordenite as that used in Example 1, in its NH$_4^+$ form. It thus had an Si/Al ratio of 5.2 and a sodium content of less than 50 ppm. In this example, 50 g of the prepared mordenite firstly underwent dry impregnation with 60 ml of an aqueous solution containing 38.8 g of Ce(NO$_3$)$_3$.6H$_2$O. The modified mordenite was then finally calcined in dry air at 550° C. for 4 hours.

The solid obtained after these treatments was given the reference HMCe2. The cerium content was 25% by weight with respect to the zeolite.

The steps of mixing the mordenite and alumina, dispersion of platinum, forming, reduction of the catalyst and the isomerization test conditions were identical to those described in Example 1.

The performance of catalyst C2 (in which the platinum content was about 0.12%) is shown in Table I.

Example 3: Catalyst C3, in accordance with the invention

The raw material used was the same mordenite as that used in Example 1, in its NH$_4^+$ form. It thus had an Si/Al ratio of 5.2 and a sodium content of less than 50 ppm. In this example, the modified mordenite was first calcined in dry air at 550° C. for 4 hours. 50 g of the prepared mordenite then underwent dry impregnation with 60 ml of an ethanolic solution containing 22 g of Ce(C$_5$H$_7$O$_2$)$_3$.3H$_2$O (Ce(III) 2,4-pentanedione). The above cycle of operations was then repeated once more. The modified mordenite was then finally calcined in dry air at 550° C. for 4 hours.

The solid obtained after these treatments was given the reference HMCe3. The cerium content was 25% by weight with respect to the zeolite.

The steps of mixing the mordenite and alumina, dispersion of platinum, forming, reduction of the catalyst and the isomerization test conditions were identical to those described in Example 1.

The performance of catalyst C3 (in which the platinum content was about 0.12%) is shown in Table I.

Example 4: Catalyst C4, not in accordance with the invention

Catalyst C4 contained the mordenite, in the H form, with a global Si/Al ratio of 5.2 used for the preparation of catalysts C1, C2 and C3. However, in this example the mordenite was not modified in accordance with the invention.

The steps of mixing the mordenite and alumina, dispersion of platinum, forming, reduction of the catalyst and the isomerization test conditions were identical to those described in Example 1.

The performance of catalyst C4 (in which the platinum content was about 0.12%) is shown in Table I where it is compared with catalysts C 1, C2 and C3 of the invention.

TABLE I

| | Effect of treatments on the selectivities at iso-approximate equilibrium | | | |
| --- | --- | --- | --- | --- |
| Catalysts | C1 according to invention | C2 according to invention | C3 according to invention | C4, not according to invention |
| Example | 1 | 2 | 3 | 4 |
| AEQ o-xylene, % | 94.3 | 94.6 | 94.4 | 94.7 |
| C8 aromatics + naphthenes, % yield | 93.9 | 94.2 | 94.1 | 92.2 |
| Dismutation, % | 2.7 | 2.4 | 2.6 | 4.4 |

Table I describes the performance of catalysts C1, C2 and C3 comprising the selective mordenite of the invention. The effect on the selectivities of the modifications by dry impregnation of cerium salts is particularly clear.

Catalysts C1, C2 and C3 of the invention performed better than catalyst C4 of the prior art. At iso-approximate equilibrium of o-xylene, the isomerisation yield for C8 aromatics+naphthenes obtained for catalysts C1, C2 and C3 was superior to that of catalyst C4 which did not conform with the invention. In the case of the mordenites which had been rendered selective in accordance with the invention (catalysts C1, C2 and C3), the secondary dismutation reactions of the xylenes and ethylbenzene to produce, inter alia, trimethylbenzenes, were greatly inhibited with respect to that obtained in the presence of non selective mordenite (catalyst C4).

Example 5: Catalyst C5, in accordance with the invention

The raw material was a mordenite with a global Si/Al ratio of 10.5, a lattice Si/Al ratio, measured using infra-red, of 11.2, a sodium content with respect to the weight of dry mordenite of about 3.8%, an elemental cell volume of 2.755 $nm^3$, a pore volume in nitrogen, measured at $-196°$ C. and at $P/P_0=0.19$, of 0.21 $cm^3$ of liquid per gram of mordenite, and a specific surface area, measured by the B.E.T. method, of 480 $m^2/g$.

The mordenite firstly underwent 3 ion exchange runs in a solution of 10N $NH_4NO_3$ at about 100° C., for 4 hours for each exchange run. The weight content of sodium measured after this treatment was less then 50 ppm.

The $NH_4^+$ form of mordenite obtained above was then calcined in dry air for 4 hours at 500° C. 50 g of the prepared mordenite was then dry impregnated with 60 ml of an ethanolic solution containing 15.5 g of the salt $Ce(NO_3)_3 \cdot 6H_2O$. The operations described above were then repeated once more. Finally, the modified mordenite was calcined in dry air at 550° C. for 4 hours.

The solid obtained following these treatments was given the reference HMCe5. The cerium content was 20% by weight with respect to the zeolite.

The latter was intimately mixed with alumina on which 0.3% by weight of platinum had been dispersed. The product constituted by the mixture of HMCe5 mordenite+alumina contained 40% by weight of alumina. The platinum content in the final catalyst (containing HMCe5) was thus about 0.12% by weight.

The catalyst produced was then formed by pelletization, calcined in air at 550° C. for 2 hours and reduced in hydrogen at 500° C. for 3 hours.

Catalyst C5 produced was tested by isomerisation of a mixture of ortho-xylene (80% by weight) and ethylbenzene (20% by weight) at a temperature of 410° C., at a pressure of 1.2 MPa, a space velocity (wwh) of 10 $(hour)^{-1}$ and a hydrogen to hydrocarbons ratio ($H_2/HC$) of about 4.

The performances of catalyst C5 (and the catalysts prepared in the following examples) are shown in Table II.

Example 6: Catalyst C6, not in accordance with the invention

Catalyst C6 contained the H form of the mordenite, with a global Si/Al ratio of 10.5, used to prepare catalyst C5. However, in this treatment, no modification treatment in accordance with the invention was carried out.

The steps of mixing the mordenite and alumina, dispersion of platinum, forming, reduction of the catalyst and the isomerisation test conditions were identical to those described in Example 5.

The performance of catalyst C6 (in which the platinum content was about 0.12%) is shown in Table II.

TABLE II

Effect of treatments at iso-approximate equilibrium

| Catalysts | C5, according to invention | C6, not according to invention |
|---|---|---|
| Example | 5 | 6 |
| AEQ o-xylene, % | 95.2 | 95.5 |
| C8 aromatics + naphthenes yield, % | 83.8 | 80.6 |
| Dismutation, % | 6.5 | 10.2 |

Table II describes the performance of catalyst C5 in accordance with the invention and catalyst C6, which had not been modified in accordance with the invention. The effect on the selectivities of the modifications by dry impregnation of cerium salts is particularly clear.

Catalyst C5 of the invention performed better than catalyst C6 of the prior art. At iso-approximate equilibrium of o-xylene, the isomerization yield for C8 aromatics+ naphthenes obtained for catalyst C5 was superior to that of catalyst C6 which did not conform with the invention. In the case of the catalyst comprising mordenite which had been rendered selective in accordance with the invention (catalyst C5), secondary dismutation reactions of the xylenes and ethylbenzene to produce, inter alia, trimethylbenzenes, were greatly inhibited with respect to that obtained in the presence of non selective mordenite (catalyst C6).

The preceding examples can be repeated with similar success by substituting the generically or specifically described reactants and/or operating conditions of this invention for those used in the preceding examples.

The entire disclosure of all applications, patents and publications, cited above and below, and of corresponding French application 95/09.058, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the isomerization of an aromatic $C_8$ cut containing xylenes, at a temperature of 240–600° C., a pressure of 0.05–10 MPa, at a space velocity of 0.5–200 $h^{-1}$ and a hydrogen/hydrocarbons molar ratio of 0.5–12, in the presence of a catalyst containing a matrix, a mordenite, cerium and at least one metal from group VIII, wherein the catalyst contains 1.89–97.89% of the matrix, 2–98% by weight of the mordenite, 0.1–40% by weight of the cerium, and 0.01–3% by weight of the at least one metal from group VIII, the percentages being with respect to the total catalyst weight, and the cerium is introduced into the catalyst by impregnation.

2. A process according to claim 1, operating at a temperature of 350–510° C., a pressure of 0.2 to 3 MPa, at a space velocity of 2–100 $h^{-1}$ and a hydrogen/hydrocarbons molar ratio of 2 to 6.

3. A process according to claim 1 or claim 2, in which the catalyst contains 2–98% by weight of mordenite, 0.1–40% by weight of cerium, and 0.01–3% by weight of at least one metal from group VIII, the percentages being with respect to the total catalyst weight.

4. A process according to claim 1, in which the catalyst contains 7–40% by weight of cerium.

5. A process according to claim 1, in which the cerium is deposited on the mordenite.

6. A process according to claim 1, in which the mordenite is a large pore mordenite with an Si/Al atomic ratio in the range 4.5 to 100.

7. A process according to claim 1, in which the matrix is selected from the group constituted by alumina, magnesia, silica-alumina and clays.

8. A process according to claim 1, in which the group VIII metal is selected from the group constituted by palladium and platinum.

9. A process according to claim 1, wherein the mordenite comprises less than 2000 ppm of sodium, the Si/Al ratio is in the range of 4.5:1 to 100:1 for large pore mordenites and 4.0:1 to 100:1 for small pore mordenites, and wherein the mordenite is treated by:

(1) calcining the mordenite in the $NH^4$ form at 450–550° C. in dry air or an inert gas, (2) dry impregnating the calcined mordenite with a cerium salt solution, and drying the solid, and (3) calcining resultant dried mordenite at 350–600° C. in dry air for 4 hours to 36 hours.

10. A process according to claim 9, wherein the mordenite contains less than the 500 ppm of sodium, the Si/Al for large mordenites is 4.5:1 to 20:1, the Si/Al for small pore mordenites is 4:1 to 7:1, and the calcining of the dried mordenite is conducted at 450° C. to 550° C.

11. A process according to claim 1, wherein the cerium is impregnated into the catalyst by dry impregnation with a cerium salt solution.

12. A process according to claim 1, wherein the catalyst consists of matrix, mordenite, cerium and at least one group VIII metal.

13. A process for the isomerization of an aromatic $C_8$ cut containing xylenes, under effective isomerization conditions, in the presence of a catalyst containing a matrix, a mordenite, cerium and at least one metal from group VIII, wherein the catalyst contains 1.89–97.89% of the matrix, 2–98% by weight of the mordenite, 0.1–40% by weight of the cerium, and 0.01–3% by weight of the at least one metal from group VIII, the percentages being with respect to the total catalyst weight, and the cerium is introduced into the catalyst by impregnation.

14. A process for the isomerization of an aromatic $C_8$ cut containing xylenes, under effective isomerization conditions, in the presence of a catalyst consisting of a matrix, a mordenite, cerium and at least one metal from group VIII, wherein the catalyst contains 1.89–97.89% of the matrix, 2–98% by weight of the mordenite, 0.1–40% by weight of the cerium, and 0.01–3% by weight of the at least one metal from group VIII, the percentages being with respect to the total catalyst weight, and the cerium is introduced into the catalyst by impregnation.

15. A process according to claim 13 wherein the cerium is impregnated into the catalyst by dry impregnation with a cerium salt solution.

* * * * *